United States Patent [19]

Chambers et al.

[11] Patent Number: 5,604,240
[45] Date of Patent: Feb. 18, 1997

[54] PYRROLO-PYRIDINE DERIVATIVES

[75] Inventors: Mark S. Chambers, Puckeridge, England; Victor G. Matassa, Velletri, Italy

[73] Assignee: Merck, Sharp & Dohme, Ltd., Hoddesdon, England

[21] Appl. No.: 559,320

[22] Filed: Nov. 16, 1995

[30] Foreign Application Priority Data

Nov. 21, 1994 [GB] United Kingdom .................. 9423460

[51] Int. Cl.⁶ ...................... A61K 31/435; C07D 471/04
[52] U.S. Cl. ............................................. 514/300; 546/113
[58] Field of Search .............................. 546/113; 514/300

[56] References Cited

U.S. PATENT DOCUMENTS 5,298,520  3/1994  Baker et al. ............................ 514/383
5,432,177  2/1995  Baker et al. ............................ 514/253

FOREIGN PATENT DOCUMENTS

0438230A2  7/1991  European Pat. Off. .
0494774A1  7/1992  European Pat. Off. .
0497512A2  8/1992  European Pat. Off. .
WO93/18029  9/1993  WIPO .
WO94/02477  2/1994  WIPO .
WO94/03446  2/1994  WIPO .

*Primary Examiner*—Bernard Dentz
*Attorney, Agent, or Firm*—Robert J. North; Melvin Winokur

[57] ABSTRACT

A class of substituted pyrrolo[2,3-c]pyridine derivatives are selective agonists of 5-HT$_1$-like receptors and are therefore useful in the treatment of clinical conditions, in particular migraine and associated disorders, for which a selective agonist of these receptors is indicated.

5 Claims, No Drawings

PYRROLO-PYRIDINE DERIVATIVES

The present invention relates to a class of substituted pyrrolo[2,3-c]pyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309-11).

The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the pyrrolo[2,3-c]pyridine derivatives provided by the present invention.

The present invention provides a compound of formula I, or a salt or prodrug thereof:

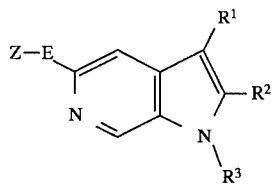

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

R$^1$ represents —CH$_2$·CHR$^4$·NR$^6$R$^7$, or a group of formula (a), (b), (c), (d), (e), (f) or (g):

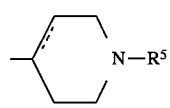

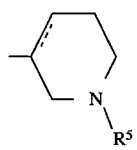

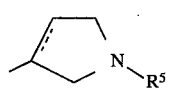

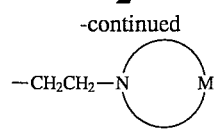

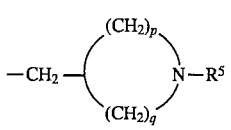

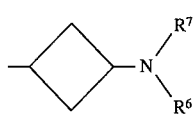

in which the broken line represents an optional chemical bond;

M represents the residue of an azetidine, pyrrolidine or piperidine ring;

p is zero or 1 and q is an integer from 1 to 4, provided that the sum of p+q is 2, 3 or 4; and R$^2$, R$^3$, R$^4$, R$^5$, R$^6$ and R$^7$ independently represent hydrogen or C$_{1-6}$ alkyl.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "C$_{1-6}$ alkoxy", "C$_{1-6}$ alkylthio" and "C$_{1-6}$ alkylamino" are to be construed accordingly.

The expression "C$_{2-6}$ alkenyl" as used herein refers to straight-chained and branched alkenyl groups containing from 2 to 6 carbon atoms. Typical examples include vinyl and allyl groups.

The expression "C$_{2-6}$ alkynyl" as used herein refers to straight-chained and branched alkynyl groups containing from 2 to 6 carbon atoms. Typical examples include ethynyl and propargyl groups.

Typical C$_{3-7}$ cycloalkyl groups include cyclopropyl, cyclobutyl, cyclopentyl and cyclohexyl.

Typical aryl groups include phenyl and naphthyl.

The expression "aryl(C$_{1-6}$)alkyl" as used herein includes benzyl, phenethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hych-ochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. In addition, the compounds of formula I above wherein $R^1$ represents a group of formula (g) may exist as discrete isomers in which the $-NR^6R^7$ group is either cis or trans to the other substituent on the cyclobutane ring. It is to be understood that all such isomers and mixtures thereof in any proportion are encompassed within the scope of the present invention.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E represents a straight or branched alkylene chain, this may be, for example, methylene, ethylene, 1-methylethylene, propylene, 2-methylpropylene or butylene. In addition, E may represent a chemical bond such that the moiety Z is attached directly to the pyrrolo[2,3-c]pyridine ring system.

When $R^1$ represents $-CH_2 \cdot CHR^4 \cdot NR^6R^7$ or a group of formula (a), (b), (c) or (d), representative values include aminoethyl, N-methylaminoethyl, N,N-dimethylaminoethyl, 4-piperidinyl, 1-methyl-4-piperidinyl, 1,2,5,6-tetrahydropyridin-4-yl, 1-methyl-1,2,5,6-tetrahydropyridin-4-yl, 3-pyrrolidinyl, 1-methyl-3-pyrrolidinyl, 3-azetidinyl and 1-methyl-3-azetidinyl. Particular values include N,N-dimethylaminoethyl, 1-methyl-4-piperidinyl and 1-methyl-1,2,5,6-tetrahydopyridin-4-yl.

In another embodiment, $R^1$ represents a group of formula (e) in which M represents the residue of an azetidine or pyrrolidine ring. Thus, $R^1$ suitably represents the azetidin-1-ylethyl or pyrrolidin-1-ylethyl moiety.

When $R^1$ represents a group of formula (f), the resulting group is an azetidin-2-ylmethyl, azetidin-3-ylmethyl, pyrrolidin-2-ylmethyl, pyrrolidin-3-ylmethyl, piperidin-2-ylmethyl or pipefidin-3-ylmethyl group, in particular an azetidin-3-ylmethyl or pyrrolidin-2-ylmethyl group, substituted on the ring nitrogen atom by the group $R^4$.

The group $R^1$ of formula (g) is suitably 3-aminocyclobutyl, 3-(N-methylamino)cyclobutyl or 3-(N,N-dimethylamino)cyclobutyl, especially cis- or trans-3-(N,N-dimethylamino)cyclobutyl.

Suitable values for the groups $R^2$ to $R^7$ include hydrogen and methyl. Preferably, $R^2$, $R^3$ and $R^4$ are each hydrogen.

A particular sub-class of compounds according to the invention is represented by the compounds of formula II, and salts and prodrugs thereof:

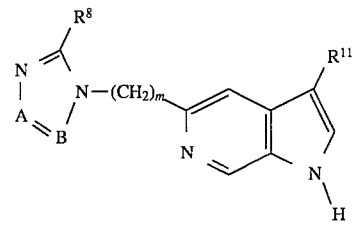

wherein m is zero, 1, 2 or 3, preferably zero or 1;

A represents nitrogen or CH;

B represents nitrogen or C-$R^9$;

$R^8$ and $R^9$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and $R^{11}$ represents $-CH_2 \cdot CH_2 \cdot NR^6R^7$, in which $R^6$ and $R^7$ are as defined with reference to formula I above; or a group of formula (a) as defined with reference to formula I above.

Particular values of $R^8$ and $R^9$ include hydrogen, methyl, ethyl, benzyl and amino, especially hydrogen.

Particular values of $R^{11}$ include N,N-dimethylaminoethyl, 1-methyl-4-piperidinyl and 1-methyl-1,2,5,6-tetrahydropyridin-4-yl.

Specific compounds within the scope of the present invention include:

N-methyl-1,2,5,6-tetrahydro-4-[5-(1,2,4-triazol-1-yl)-1H-pyrrolo[2,3-c]-pyridin-3-yl]pyridine;

N-methyl-4-[5-(1,2,4-triazol-1-yl)-1H-pyrrolo[2,3-c]pyridin-3-yl]piperidine; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, steatic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compouncled to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/Kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises the cyclization of a compound of formula III:

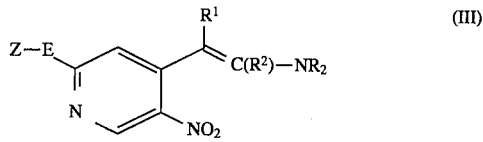

wherein Z, E, $R^1$ and $R^2$ are as defined above, and R represents $C_{1-4}$ alkyl, especially methyl; followed by attachment of the group $R^3$, where this is other than hydrogen, by conventional N-alkylation methods.

The cyclization of compound III is conveniently brought about under catalytic hydrogenation conditions. This is suitably effected by treating compound III with hydrogen in the presence of a catalyst such as platinum oxide, typically in a solvent such as ethanol, advantageously under elevated pressure.

In an alternative procedure, the compounds of formula I wherein $R^1$ represents a group of formula (a) as defined above, in which the broken line represents a chemical bond, may be prepared by a process which comprises reacting a compound of formula IV with a compound of formula V:

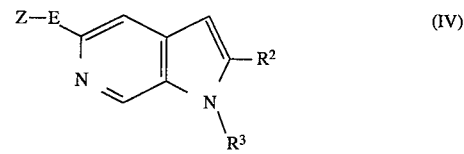

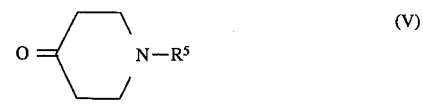

wherein Z, E, $R^2$, $R^3$ and $R^5$ are as defined above.

The reaction is conveniently effected under basic conditions, e.g. potassium hydroxide in methanol, typically under reflux.

The intermediates of formula IV may be prepared by cyclization of a compound of formula III above wherein $R^1$ is hydrogen, under conditions analogous to those described above for the cyclization of the compounds of formula III.

Where they are not commercially available, the starting materials of formula III and V, as well as the intermediates of formula III above wherein $R^1$ is hydrogen, may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by teclmiques known from the art. For example, a compound of formula I wherein $R^1$ represents a group of formula (a), in which the broken line represents a chemical bond, initially obtained may be converted into the corresponding compound in which the broken line is absent by conventional catalytic hydrogenation, which typically comprises treating the appropriate compound with hydrogen in the presence of a catalyst such as platinum oxide, in a suitable solvent such as ethanol, optionally with the addition of a mineral acid such as 2M hydrochloric acid, and advantageously under elevated pressure. Moreover, a compound of formula I wherein $R^3$ is hydrogen initially obtained may be converted into a compound of formula I wherein $R^3$ represents $C_{1-6}$ alkyl by standard alkylation teclmiques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional teclmiques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P.G.M. Wuts, *Protective Groups in Orgasmic Synthesis*, John Wiley & Sons, 1991. The protecting groups may be removed at a convenient subsequent stage using methods known from the art.

The following Examples illustrate the preparation of compounds according to the invention.

EXAMPLE 1

N-Methyl-1,2,5,6-tetrahydro-4-[5-(1,2,4-triazol-1-yl)-1H-pyrrolo[2,3-c]pyridin-3-yl]pyridine 1. Intermediate 1:5-(1,2,4-Triazol-1-yl)- 1H-pyrrolo[2,3-c]pyridine a) 4-Methyl-5-nitro-2-(1,2,4-triazol-1-yl)pyridine To a solution of 1,2,4-triazole (4.0 g, 58 mmol) in dry DMF (20 mL) was added potassium carbonate (12.0 g, 87 mmol) and 2-chloro-4-methyl-5-nitropyridine (10 g, 58 mmol) and the mixture stirred at ambient temperature under nitrogen for 24 hours. Ethyl acetate (500 mL) and water (250 mL) were added to the mixture and the resulting precipitate was collected by filtration to give the title compound (5.08 g, 43%) as a pale brown solid. The filtrate was separated and the organic phase was washed with water (250 mL) and brine (250 mL), dried (MgSO$_4$) and evaporated. The residue was triturated with ethyl acetate and the precipitate collected by filtration to give the title compound as a brown solid (4.11 g, 35%, overall yield 78%). mp 198°–200° C. $^1$NMR (360 MHz, CDCl$_3$) δ2.72 (3H, s), 7.86 (1H, s), 8.07 (1H, s) 9.03 (1H, s) and 9.15 (1H, s).

b) N,N-Dimethyl-2-(5-nitro-2-(1,2,4-triazol-1-yl)-pyridin-4-yl)ethenamine

To a suspension of 4-methyl-5-nitro-2-(1,2,4-triazol-1-yl)pyridine (4.1 g, 20 mmol) in dry DMF (30 mL) was added dimethylformamide dimethyl acetal (5.9 mL, 44 mmol) and the mixture heated at 90° C. for 20 min. The solvent was evaporated evaporated in vacuo using toluene as an azeotrope to give the title compound (5.2 g, 100%) as a dark red solid. mp 225°–228° C. $^1$NMR (360 MHz, CDCl$_3$)δ3.10 (6H, s) 6.13 (1H, d, J=13.1 Hz), 7.54 (1H, d, J=13.1 Hz), 7.81 (1H, s) 8.04 (1H, s), 8.92 (1H, s) and 9.17 (1H, s).

c) 5-(1,2,4-Triazol-1-yl)-1H-pyrrolo[2,3-c]pyridine

N,N-Dimethyl-2-(5-nitro-2-(1,2,4-triazol-1-yl)pyridin-4-yl)ethenamine (8 g, 31 mmol) was hydrogenated over platinum oxide (1.6 g) in ethanol (150 mL) at 30 psi of hydrogen for 1 hour. The catalyst was removed by filtration and the solvent evaporated in vacuo. The residue was chromatographed on silica eluting with ethyl acetate to afford an orange/brown solid. This was triturated with ether and the precipitate collected by filtration to give the title compound (2.89 g, 51%) as a pink solid. mp 203°–205° C. $^1$H NMR (360 MHz, d$_6$-DMSO)δ6.67 (1H, d, J=3.0 Hz), 7.76 (1H, d, J=2.9 Hz), 8.01 (1H, s), 8.23 (1H, s), 8.70 (1H, s), 9.25 (1H, s) and 11.86 (1H, br s).

2. N-Methyl-1,2,5,6-tetrahydro-4-[5-(1,2,4-triazol-1-yl)-1H-pyrrolo[2,3-c]pyridin-3-yl]pyridine A mixture of Intermediate 1 (0.22 g, 1.2 mmol)and N-methyl-4-piperidone (0.18 mL, 1.5 mmol) was heated in potassium hydroxide in methanol (2M, 5 mL) at reflux for 16 hours. Further N-methyl-4-piperidone (34 µL, 0.3 mmol) was added and the mixture heated at reflux for another 3 hours. The solvent was evaporated in vacuo and the residue chromatographed on silica eluting with a gradient of 90:10:1 to 80:20:1, DCM:MeOH:NH$_3$ to afford an orange solid. This was triturated with ether and the solid collected by filtration to give the title compound (0.2 g, 60%) as a beige solid. mp 220° C. (dec.). Found: C, 62.61; H, 5.69; N, 28.62. C$_{15}$H$_{16}$N$_6$·0.5(H$_2$O) requires C, 62.27; H, 5.92; N, 29.05%. $^1$H NMR (360 MHz, d$_6$-DMSO)δ2.30 (3H, s), 2.52–2.64 (4H, m), 3.07–3.12 (2H, m), 6.15–6.19 (1H, m), 7.81 (1H, s), 8.16 (1H, s), 8.24 (1H, s), 8.66 (1H, s), 9.27 (1H, s) and 11.92 (1H, br s).

EXAMPLE 2

N-Methyl-4-[5-(1,2,4-triazol-1-yl)-1H-pyrrolo[2,3-c]pyridin-3-yl]piperidine

N-Methyl-1,2,5,6-tetrahydro-4-[5-(1,2,4-triazol-1-yl)-1H-pyrrolo[2,3-c]pyridin-3-yl]pyridine (0.2 g, 0.7 mmol) was hydrogenated over platinum oxide (0.2 g) in ethanol (40 mL) with HCl (2M, 36 µL, 0.71 mmol) at 40 psi of hydrogen for 6 hours. The catalyst was removed by filtration and the solvent evaporated in vacuo. The residue was redissolved in ethanol:water, 10:1 (40 mL) and hydrogenated over platinum oxide (0.3 g) at 40 psi of hydrogen for 3 hours. The catalyst was removed by filtration and the residue chromatographed on silica eluting with 90:10:1, DCM:MeOH:NH$_3$ to give a colourless gum. This was triturated with ether and the solid collected by filtration to give the title compound (56 mg, 28%) as a colourless solid. mp 209°–211° C. Found: C, 62.86; H, 6.31; N, 29.07. C$_{15}$H$_{18}$N$_6$·0.25(H$_2$O) requires C, 62.81; H, 6.50; N, 29.30%. $^1$H NMR (360 MHz, d$_6$-DMSO)δ1.68–1.80 (2H, m), 1.87–1.95 (2H, m), 2.00–2.10 (2H, m), 2.21 (3H, s), 2.75–2.92 (3H, m), 7.54 (1H, s), 7.98 (1H, s), 8.22 (1H, s), 8.65 (1H, s), 9.24 (1H, s) and 11.61 (1H, br s).

We claim:

1. A compound of formula I, or a salt or prodrug thereof:

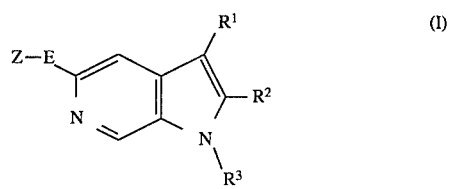

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing front 1 to 4 carbon atoms;

$R^1$ represents $-CH_2 \cdot CHR^4 \cdot NR^6 R^7$, or a group of formula (a), (b), (c), (d), (e), (f) or (g):

(a) [structure: cyclohexene with N—$R^5$]

(b) [structure: cyclohexene with N-$R^5$]

(c) [structure: cyclopentene with N-$R^5$]

(d) [structure: cyclobutane with N—$R^5$]

(e) $-CH_2CH_2-N$ [ring] M (f) $-CH_2-$ [bicyclic structure with $(CH_2)_p$, $(CH_2)_q$, N—$R^5$]

(g) [structure: cyclobutane with N($R^7$)($R^6$)]

in which the broken line represents an optional chemical bond;

M represents the residue of an azetidine, pyrrolidine or piperidine ring;

p is zero or 1 and q is an integer from 1 to 4, provided that the sum of p+q is 2, 3 or 4; and $R^2$, $R^3$, $R^4$, $R^5$, $R^6$ and $R^7$ independently represent hydrogen or $C_{1-6}$ alkyl.

2. A compound as claimed in claim 1 represented by formula II, and salts and prodrugs thereof:

(II) [structure of formula II with $R^8$, $R^{11}$, A, B, N-(CH$_2$)$_m$, pyrrolopyridine ring with NH]

wherein m is zero, 1, 2 or 3;

A represents nitrogen or CH;

B represents nitrogen or C-$R^9$;

$R^8$ and $R^9$ independently represent hydrogen, $C_{1-6}$alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and $R^{11}$ represents $-CH_2 \cdot CH_2 \cdot NR^6 R^7$, in which $R^6$ and $R^7$ are as defined in claim 1; or a group of formula (a) as defined in claim 1.

3. A compound selected from:

N-methyl-1,2,5,6-tetrahydro-4-[5-(1,2,4-triazol-1-yl)-1H-pyrrolo[2,3-c]-pyridin-3-yl]pyridine;

N-methyl-4-[5-(1,2,4-triazol-1-yl)-1H-pyrrolo[2,3-c]pyridin-3-yl]piperidine; and salts and prodrugs thereof.

4. A pharmaceutical composition comprising a compound of formula I as defined in claim 1 or a pharmaceutically acceptable salt thereof or a prodrug thereof in association with a pharmaceutically acceptable carrier.

5. A method for the treatment and/or prevention of clinical conditions for which a selective agonist of 5-HT$_1$-like receptors is indicated, which comprises administering to a patient in need of such treatment an effective amount of a compound of formula I as defined in claim 1 or a pharmaceutically acceptable salt thereof or a prodrug thereof.

* * * * *